United States Patent [19]

Psaros et al.

[11] Patent Number: 5,237,990
[45] Date of Patent: Aug. 24, 1993

[54] APPARATUS FOR THE ADMINISTRATION OF A RESPIRATORY GAS AND AT LEAST ONE ANAESTHETIC

[75] Inventors: Georgios Psaros, Tullinge; Rune Bergkvist, Vaxholm; Sven-Gunnar Olsson, Arloev, all of Sweden

[73] Assignee: Siemens Aktiengesellschaft, Munich, Fed. Rep. of Germany

[21] Appl. No.: 821,689

[22] Filed: Jan. 16, 1992

[30] Foreign Application Priority Data

Jan. 25, 1991 [SE] Sweden ................................ 9100228

[51] Int. Cl.[5] ............................................. A61M 16/00
[52] U.S. Cl. ............................ 128/204.21; 128/203.12; 128/204.13; 128/205.11
[58] Field of Search ..................... 128/204.21, 203.12, 128/204.13, 204.14, 204.22, 205.11, 205.13

[56] References Cited

U.S. PATENT DOCUMENTS

| | | | |
|---|---|---|---|
| 3,794,027 | 2/1974 | Johnson | 128/204.13 |
| 4,702,242 | 10/1987 | Broddner et al. | 128/205.13 |
| 4,770,168 | 9/1988 | Rusz et al. | 128/203.12 |
| 4,905,685 | 3/1990 | Olsson et al. | 128/203.12 |

FOREIGN PATENT DOCUMENTS 0166305  1/1986  European Pat. Off. .
8807876 10/1988  PCT Int'l Appl. .

Primary Examiner—William H. Grieb
Attorney, Agent, or Firm—Hill, Steadman & Simpson

[57] ABSTRACT

An apparatus for the administration of a respiratory gas and at least one anaesthetic to a living being, in which apparatus the anaesthetic is vaporized in a vaporizing unit and is entrained in respiratory gas, acquires a safer and more accurate control of the anaesthetic concentration level by means of a regulating valve which controls the flow of respiratory gas through the vaporizing unit and in that a regulating device controls the regulating valve with such accuracy that a preselected concentration of vaporized anaesthetic in the respiratory gas is substantially fully maintained. To further increase the control of the apparatus it may also be provided with a feedback system for both the anaesthetic concentration level and the total flow.

27 Claims, 2 Drawing Sheets

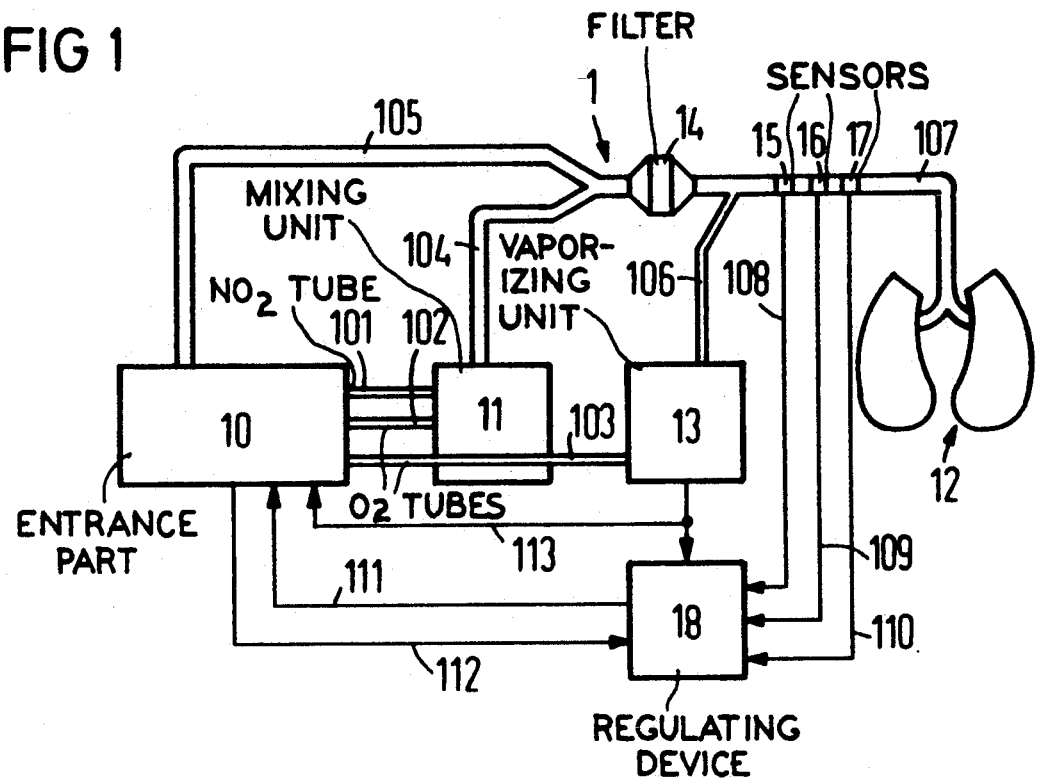
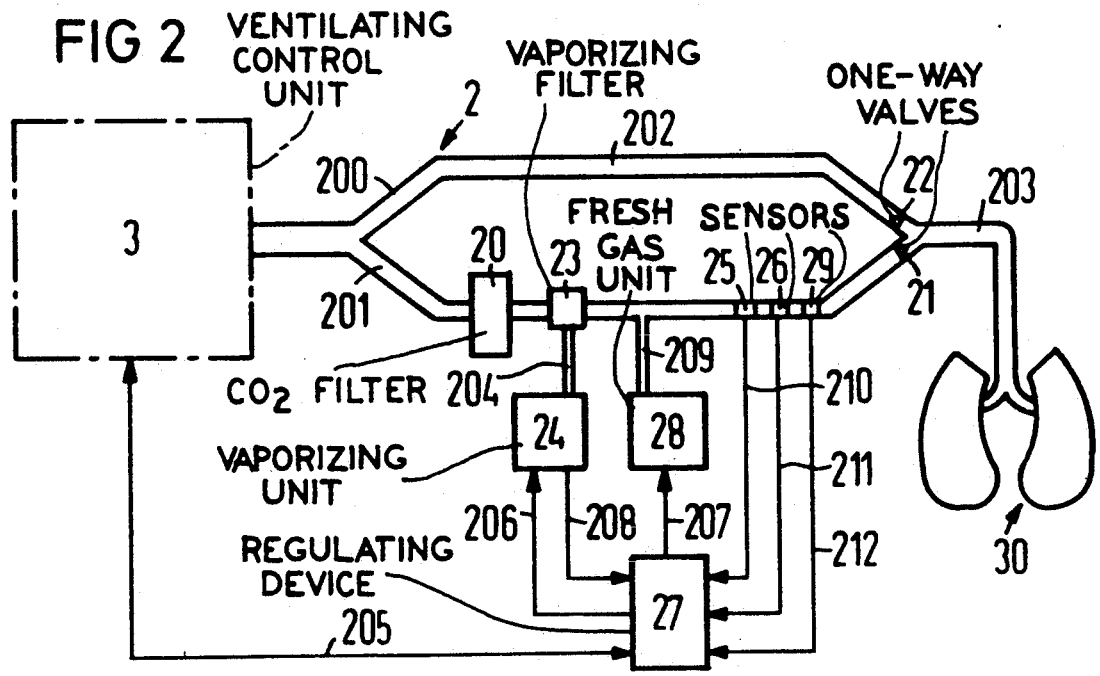

APPARATUS FOR THE ADMINISTRATION OF A RESPIRATORY GAS AND AT LEAST ONE ANAESTHETIC

BACKGROUND OF THE INVENTION

1. Field of the Invention

The invention relates to an apparatus for the administration of a respiratory gas and at least one anaesthetic to a patient.

2. Description of the Prior Art

An apparatus having a vaporizing unit which contains liquid anaesthetic, whereby a predetermined concentration of the anaesthetic in the respiratory gas is achieved by vaporizing a defined amount of the liquid anaesthetic in respiratory gas passed through the vaporizing unit is described in U.S. Pat. No. 3,794,027. The apparatus, an animal anaesthesia machine, has an entrance part via which the respiratory gas, or the gases that form the respiratory gas, is supplied to the apparatus and an inlet tube, which conducts the respiratory gas and the vaporized anaesthetic to the patient. The apparatus includes a canister to which a source of gas is connected via a vaporizer unit. The inlet tube conducts respiratory gas to the patient and an outlet tube conducts the respiratory gas from the patient via a common Y-piece. A second vaporizer unit is connected to the inlet tube. The two vaporizer units may be used separately or together and may contain the same or different anesthetics. The first vaporizer unit has a valve, which can admit the gas from the gas source through the vaporizer unit and divert the gas around the vaporizer unit. When the gas is led through the vaporizer unit, it will bubble through the liquid anaesthetic and vaporize it. The gas containing the anaesthetic is then conducted to the canister and from there to the patient. The second vaporizer unit has two hollow sections which communicate via two apertures. The first hollow section forms a part of the inlet line. A substantially triangular vane can be placed in two positions, one of which permits the gas only to pass through the first hollow section. When the vane is brought into its second position, the gas will be led into the second hollow section and pass through a wick which separates the second hollow section into two halves. The wick is partially placed in the liquid anaesthetic which has been absorbed by the wick. The gas containing anaesthetic then passes through the second aperture and out into the inlet line.

Control of the vaporization of the anaesthetic is, for both vaporizer units, performed manually by activating a switch system (valve and vane) for a defined time when vaporization shall take place. The concentration of anaesthetic depends mainly on two factors: the gas flow through the vaporizer unit, which will determine the amount of anaesthetic that is vaporized for each time unit, and the total time during which the gas is led through the vaporizer unit, which will determine the total amount of vaporized anaesthetic and thereby also the concentration. This results in a variation of the concentration during the time anaesthetic is supplied to the patient. In order to avoid concentrations that are too high or too low, an empirically established scheme for switching the vaporizer unit on and off should be followed. With this system losses of anaesthetic from the system, through leakage and such, cannot be taken into account.

Another known apparatus, described in U.S. Pat. No. 4,770,168, has a chamber with liquid anaesthetic and a positive displacement pump. Via a valve, gas can be diverted from a pipe to the chamber in which the gas becomes saturated with anaesthetic. The flow of gas from the chamber back to the pipe is controlled by the pump. By controlling the motor that drives the pump via a feedback system, depending on a total flow in the pipe or the anaesthetic concentration in the pipe, the concentration of anaesthetic may be maintained with higher accuracy than the previously described apparatus. The chamber may also include a thermistor. The motor may then also be controlled depending on the temperature in the anaesthetic chamber.

The pump in this known apparatus limits the useful range of the flow of anaesthetic saturated gas out into the pipe. This causes problems if a total flow is initially low, as is the case when small children or small animals are to be anaesthetized. Similar problems occur if the total flow is initially high. Furthermore, the required concentration level of anaesthetic may vary depending on the anaesthetic used and on the individual patient.

SUMMARY OF THE INVENTION

An object of the invention is to provide an apparatus for the administration of respiratory gas and an anaesthetic of the type having a vaporizing unit by which anaesthetic is vaporized into the respiratory gas flow, wherein the concentration of anaesthetic may be maintained with extremely high accuracy over a wide range of total respiratory gas flow.

This object is achieved in an apparatus constructed in accordance with the present invention, having a regulating valve controlling the flow of respiratory gas through the vaporizing unit and a regulating device controlling the regulating valve with such accuracy that a preselected concentration of vaporized anaesthetic in the respiratory gas is substantially fully maintained.

A regulating system generally of this type is the object of prior European patent application No. 90120843.9, corresponding to co-pending U.S. application Ser. No. 784,761, filed Oct. 30, 1991 (Olsson et al.). This regulating system can supply a gas flow in a range from approximately 0.6 ml/minute up to 18 liters/minute with an accuracy of better than ±1% of the selected flow.

The system in the co-pending application permits an exact portion of the total gas flow to be led to the vaporizing unit, become saturated with anaesthetic and be led back to the main gas flow resulting in a total gas flow with a very accurate concentration level of the anaesthetic.

The apparatus in the co-pending application is improved in accordance with the principles of the present invention in that the vaporizing unit has a thermal control device which controls the temperature in the vaporizing unit and maintains it at a preselected level. Because the saturation level depends on the temperature, the concentration can be maintained with even higher accuracy if the temperature in the vaporizing unit is kept at a constant temperature.

Alternatively this result may be obtained by providing the vaporizing unit with a thermistor for measuring the temperature in the vaporizing unit, the thermistor being connected to the regulating device, and the regulating device varying the flow of respiratory gas through the vaporizing unit depending on the measured temperature.

A further improvement of the apparatus according to the invention includes a first sensor for measuring the concentration of the anaesthetic in the respiratory gas located between the vaporizing unit and the patient, the first sensor being connected to the regulating device, and the regulating device controls the flow of respiratory gas depending on the measured concentration of anaesthetic.

By placing the first sensor after the vaporizing unit, preferably as close as possible to the patient, feedback of the signal corresponding to the actual concentration, and control the vaporization of the liquid anaesthetic by means of the regulating device, the system is provided not only with a means of further increasing the accuracy, but also with a control or safety system which increases the use of the apparatus.

The apparatus maintains an equally high accuracy of the concentration whether the respiratory gas is led to bubble through the liquid anaesthetic, is led through a wick which has absorbed liquid anaesthetic, or is led over the surface of the liquid anaesthetic.

In accordance with the invention there are a number of advantageous improvements in the apparatus, some of which will be described below.

With a flow sensor located in the inlet tube for measuring the total flow of respiratory gas, including the vaporized anaesthetic, the regulating system can be provided with a further parameter for increasing the accuracy. The flow sensor also provides for the possibility of controlling the total respiratory gas flow more accurately because the contribution to the flow of the vaporized anaesthetic can thereby be compensated for. To achieve this, the apparatus includes a control unit which, depending on a measured flow, controls the entrance part so that the difference between the flow supplied to the living being and a preselected flow is minimized.

The safety of the apparatus is increased in that a control signal from the regulating device superimposes a basic signal corresponding to the preselected concentration of the anaesthetic, whereby the superimposed control signal increases the accuracy of the regulating valve. Even if there should be a failure in one or several of the sensors or if the regulating device were to malfunction, cease operating, the basic signal would still guarantee the maintenance of a concentration of anaesthetic that is harmless for patients connected to the apparatus. It is an advantage to use a microprocessor as the regulating device.

An alarm function for the concentration of anaesthetic is provided in the form of a second sensor for measuring the concentration of the anaesthetic in the respiratory gas located in the inlet tube, in the vicinity of the first sensor, and a supervising unit gives an alarm if the concentration of anaesthetic falls outside a predetermined interval around the preselected value.

The object of the invention is also achieved in an embodiment of the apparatus having a first sensor, located between the vaporizing unit and a patient, which measures the concentration of the vaporized anaesthetic in the respiratory gas, and a regulating device which controls the vaporization of the vaporizing unit depending on the measured concentration so that the amount of liquid anaesthetic being vaporized minimizes the difference between the predetermined and the measured concentration of anaesthetic in the respiratory gas.

By placing the first sensor after the vaporizing unit, preferably as close as possible to the patient, feeding back the signal corresponding to the actual concentration, and controlling the vaporization of the anaesthetic by means of a regulating device, a safe and advantageous control of the concentration of anaesthetic is obtained. Even a small deviation from a preselected concentration level brings about an increase or decrease of vaporization in the vaporizing unit. It is suitable to allow a deviation of, for instance, 1% from the preselected concentration level in order not to require continual infinitesimal adjustments.

There are basically three systems which can be used for administration of anaesthetic to a patient. First is a non-rebreathing system in which all gases that are supplied to the patient are evacuated from the system after expiration. Second is a semi-rebreathing system in which the anaesthetic is continuously recirculated to the patient while all other gases are evacuated. Finally, there is a rebreathing system, in which all gases, except expired carbon dioxide, are continuously recirculated to the patient.

Whereas the apparatus previously described is preferably used in non-rebreathing or semi-rebreathing systems, the apparatus according to the second embodiment may be used in all three systems.

For the latter apparatus there are three different advantageous types of vaporizing units. In the first the respiratory gas which is led to the vaporizing unit is led through the liquid anaesthetic. The respiratory gas which thereby becomes saturated with anaesthetic is then led through a connecting tube to the inlet tube where it mixes with the main flow of the respiratory gas before entering the living being. The regulating device controls the flow of respiratory gas led through the vaporizing unit. The distance between the connection point of the connecting tube and the inlet tube and the first sensor should be large enough to allow a complete mixing of the gases before the concentration is measured. At the same time the distance should be as small as possible so that the regulating device may receive information about the actual concentration level as quickly as possible.

The second type of a vaporizing unit has a throttle valve which causes a pressure on the liquid anaesthetic that forces an amount of the liquid to mix with the respiratory gas, whereby it vaporizes, and a connecting tube which leads the respiratory gas with the vaporized anaesthetic to the inlet tube. The pressure difference across the throttle valve is, for a constant respiratory gas flow, only dependent on the position of the throttle valve. The vaporization of liquid anaesthetic depends only on the pressure difference. An accurate adjustment of the position of the throttle valve, controlled by the regulating device, will therefore maintain the selected concentration level.

The third type of a vaporizing unit has a vaporizing unit with a filter to which liquid anaesthetic is supplied, whereby the liquid anaesthetic is vaporized by the respiratory gas passing through the filter. Unlike the second vaporizer unit according to the prior art description, in which the liquid anaesthetic was absorbed by a wick and vaporized by the respiratory gas flowing through the wick, in the third type of vaporizing unit, it is possible to supply only the required amount of liquid anaesthetic to the filter. This achieves a very accurate regulation of the anaesthetic concentration level. Even if the respiratory gas flowing through the filter due to any kind of failure in the apparatus should increase, the vaporized amount of anaesthetic would remain constant. When supplying larger amounts of liquid anaesthetic to the filter it should be heated as the vaporization heat is taken from the filter itself.

In accordance with the invention there are a number of advantageous improvements in the apparatus, some of which are described below.

For the first two types of vaporizing units, to further increase the accuracy, only a part of the total respiratory gas flow is led through the vaporizing unit while the rest of the respiratory gas is conducted directly from the entrance part to the inlet tube.

Also for this embodiment, the use of a flow sensor in the inlet tube provides for a more safe and accurate apparatus.

When an anaesthetized patient is to be awakened, or if an unwanted increase in the concentration of anaesthetic in spite of all precautions has occurred, it is an advantage to have a fresh gas tube connected to the inlet tube nearby the patient, through which fresh gas tube a respiratory gas or an additional gas may be supplied to the patient without first passing through the entrance part. The supply via the fresh gas tube is controlled by the regulating device so that the predetermined total flow is maintained. If the flow from the entrance part is replaced with a flow via the fresh gas tube, the concentration of anaesthetic is quickly reduced to 0%.

The safety of the apparatus is increased by providing a control signal from the regulating device which superimposes a basic signal, corresponding to the previously selected concentration of the anaesthetic, on the current signal. Even if there should be a failure in one or several of the sensors or if the regulating device were to malfunction, the basic signal would still guarantee the maintenance of a concentration level of the anaesthetic that is harmless for patients connected to the apparatus. It is an advantage to use a microprocessor as the regulating device.

In order to reduce the consumption of liquid anaesthetic it is an advantage to use a filter for the absorption and desorption of the anaesthetic. The filter is preferably located in the inlet tube. Such a filter, also known as a reflector, is described in PCT application WO88/07876 and is made of a material which absorbs the anaesthetic during expiration and desorbs the anaesthetic during inspiration. When used together with a vaporizing filter, the two filters may be formed as one filter unit.

An alarm function for the concentration level is provided in the form at a second sensor for measuring the concentration of the anaesthetic in the respiratory gas located in the inlet tube, in the vicinity of the first sensor, and a supervising unit gives an alarm if the anaesthetic concentration falls outside a predetermined interval around the preselected value. The completely separated alarm function increases the safety for the patient.

BRIEF DESCRIPTION OF THE DRAWINGS

FIG. 1 is a schematic block diagram of a first embodiment of an apparatus constructed in accordance with the principles of the present invention, with the use of a semi-rebreathing system.

FIG. 2 is a schematic block diagram of a second embodiment of an apparatus constructed in accordance with the principles of the present invention, with a rebreathing system.

DESCRIPTION OF THE PREFERRED EMBODIMENTS

Figure 3:
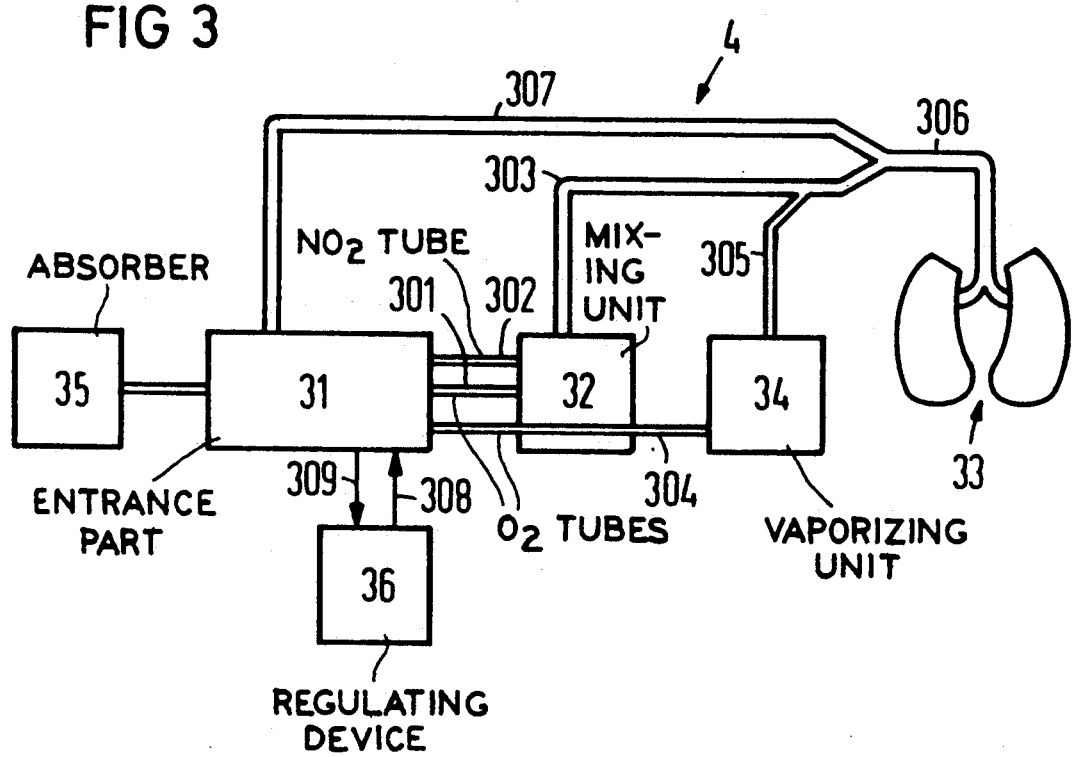
FIG. 3 is a schematic block diagram of a third embodiment of an apparatus constructed in accordance with the principles of the present invention, with a non-rebreathing system.

An embodiment of the invention is shown in FIG. 3 for use with a non-rebreathing system apparatus 4 for the administration of a respiratory gas and an anaesthetic to a patient. In the non-rebreathing system neither the respiratory gas nor the anaesthetic is recirculated back to the patient after use, as is the case in a rebreathing or semi-rebreathing system which are respectively described below in connection with the embodiments of FIGS. 1 and 2.

An entrance part 31 supplies gas, for example oxygen and nitrous oxide, to a mixing unit 32 via a first oxygen tube 301 and a nitrous oxide tube 302. In the mixing unit 32 the gases are mixed before being conducted into an inlet tube 303 leading to a patient's lungs 33. A second oxygen tube 304 connects the entrance part 31 with a vaporizing unit 34. The oxygen flow to the vaporizing unit 34 is controlled by a regulating valve in the entrance part 31. In the vaporizing unit 34 liquid anaesthetic is vaporized by the oxygen flow and the oxygen becomes saturated with anaesthetic. Through a connecting tube 305 the saturated oxygen is conducted to the inlet tube 303 and mixed with the main flow of respiratory gas before entering the lungs 33 through the patient tube 306. The patient tube 306 is common for both the inlet tube 303 and the outlet tube 307. Through the outlet tube 307 expired gas is led back to the entrance unit 31. The expired respiratory gas is then led to an absorber 35, in which anaesthetic is absorbed before the respiratory gas is evacuated.

Each gas tube 301, 302, and 304 has a regulating valve (not shown), all of the regulating valves being controlled by a regulating device 36. The regulating device 36 is connected to the entrance part 31 via a control line 308 and a signal line 309. Via the signal line 309, the regulating device 36 is provided with all information that is required in order to control the flow in each tube with highest possible accuracy, for example reference values of the flow, the position of each regulating valve, etc.

The vaporizing unit 34 has a thermal regulating device, which maintains a well-defined temperature in the vaporizing unit 34.

There are several different ways of saturating the oxygen which flows through the vaporizing unit 34 with anaesthetic. One way is to let the oxygen bubble through the liquid anaesthetic, another is to lead the oxygen through a wick soaked with the liquid anaesthetic and a third is to lead the oxygen over the surface of the liquid anaesthetic, thereby continuously exchanging saturated oxygen with unsaturated oxygen, which will become saturated due to evaporation of liquid anaesthetic. Because the saturation point is constant at constant temperatures, a high accuracy for the concentration of anaesthetic in the total respiratory gas flow is obtained by controlling the flow through the vaporizing unit 34 accurately. It is not necessary to use feedback systems where the concentration level or total respiratory gas flow are measured.

The vaporizing unit 34 may, as an alternative to the thermal regulating device, have a thermistor connected to the regulating device 36, whereby the oxygen flow through the vaporizing unit 36 will be varied depending on fluctuations in the temperature.

The apparatus 4 may also be provided with an anaesthetic sensor as an extra safety precaution. If the concentration of anaesthetic, due to any possible reason, should increase or decrease too much, an alarm will be activated.

In FIG. 1 a semi-rebreathing system apparatus 1 is described, i.e., the expired gas is not recirculated to the patient but conducted away from the patient except for the anaesthetic, which is recirculated.

In the embodiment of FIG. 1, an entrance part 10 supplies, via a nitrous oxide tube 101 and a first oxygen tube 102, a mixing unit 11 with oxygen and nitrous oxide. In the mixing unit 11 the two gases are mixed to form a respiratory gas which during inspiration is conducted to a patient's lungs 12 through an inlet tube 104. From the lungs 12 the respiratory gas is evacuated via an outlet tube 105 at the entrance part 10. When a patient is to be anaesthetized a vaporizing unit 13 is connected to the system. In the vaporizing unit 13 liquid anaesthetic, e.g., halothane, isoflurane, or enflurane, is stored. By leading oxygen through the vaporizing unit 13, liquid anaesthetic is vaporized and the oxygen is saturated with it. The vaporizing unit 13 is supplied with oxygen through a second oxygen tube 103. In FIG. 1 it is shown that the second oxygen tube 103 is led passed the mixing unit 11, so that the oxygen will not be mixed with the other gases. From the vaporizing unit 13 the oxygen and the vaporized anaesthetic are conducted through a connecting tube 106 to a patient tube 107, which is common for the inlet tube 104 and the outlet tube 105 and in which the gas flow from the mixing unit 11 and the gas flow from the vaporizing unit 13 are mixed.

Because anesthetics are expensive and, furthermore, should not be allowed to come into the operating theater where it may affect a surgeon, the apparatus 1 is provided with a filter 14 in the patient tube 107, which during expiration absorbs the anaesthetic in the expired gas and during inspiration resorbs the anaesthetic to the respiratory gas. Such a filter 14, also known as a reflector, which will be used as the designation henceforth, is described in PCT application WO88/07876.

An anaesthetic sensor 15, a flow sensor 16, and a second anaesthetic sensor 17 are located in the patient tube 107. The three sensors 15, 16, and 17 are respectively connected to a regulating device 18 via an anaesthetic signal line 108, a flow signal line 109 and an alarm signal line 110. The regulating device 18 is connected to the entrance part 10 via a control line 111 and a first reference value line 112, by which a set value of the respiratory flow is transmitted, and to the vaporizing unit 13 via a second reference value line 113, by which a set value for the concentration of anaesthetic is transmitted. The second reference line 113 also connects the entrance part 10 to the vaporizing unit 13.

When a patient is to be anaesthetized, a selected gas flow (liters/minute) and a selected relationship between oxygen and nitrous oxide is set at the entrance part 10 and a selected concentration level of anaesthetic is set at the vaporizing unit 13. The set values are transmitted to a microprocesor in the regulating unit 18 by the first reference value line 112 and second reference value line 113. The set concentration level of anaesthetic is also transmitted to a control device in the entrance part 10 via the second reference value line 113.

The control device of the entrance part 10 controls the valves which supply the nitrous oxide tube 101 and the two oxygen tubes 102 and 103 with gas. The control device controls the valves so that the set respiratory gas flow is obtained with the selected mixture of oxygen and nitrous oxide. The valve which controls the flow through the second oxygen tube 103 is set to supply an oxygen flow through the vaporizing unit 13, which is correlated to the selected concentration level of anaesthetic. Because no anaesthetic has been absorbed by the reflector 14 at this point, i.e., at the beginning of the anaesthetization, a relatively large flow of oxygen is supplied to the vaporizing unit 13 in order to build up the concentration level. Via the anaesthetic sensor 15 and the flow sensor 16, the microprocessor of the regulating device 18 receives actual values of the concentration level and the respiratory flow. By comparing these values with the reference values a control signal is determined and is transmitted via control line 111 to the entrance part 10. The determined control signal is superimposed on the control signal from the control device. A very accurate control of the set values is thus acquired at the same time as the apparatus 1 becomes relatively insusceptible to faults in the anaesthetic sensor 15 or in the microprocessor.

To compensate for the extra flow that the vaporized anaesthetic causes, the nitrous oxide flow is reduced to maintain the selected total respiratory gas flow. The reason for reducing the nitrous oxide and not the oxygen is of course that the selected oxygen concentration is more important to maintain. As an extra safety precaution the apparatus 1 has the second anaesthetic sensor 17, described above. Via the alarm signal line 110 actual values of the concentration level of the anaesthetic are transmitted to the regulating device 18. The regulating device 18 has an alarm unit, which is completely separated from the microprocessor and has the function of supervising the concentration level. If the level should fall outside a predetermined range, either lower or higher than the selected level, an alarm will be activated.

FIG. 2 shows a rebreathing system apparatus in which the expired gas is purified from carbon dioxide in a carbon dioxide filter 20 located in the inlet tube 201. The inlet tube 201 forms half of a loop 200 in a patient unit 2 of the apparatus. Inspiration and expiration are controlled by a ventilating control unit 3 indicated in dot and dash lines. At the beginning of anaesthetization, the ventilating control unit 3 functions as the entrance part and supplies the patient unit 2 with respiratory gas. As the respiratory gas is recirculated, it is only necessary to supply additional gas to compensate for losses and to maintain the selected mixture of gases and concentration of anaesthetic. The second half of the loop 200 is formed by an outlet tube 202. As in the foregoing example, a patient tube 203 is common for the inlet and outlet tubes 201 and 202. In order to control the direction of the flow of the respiratory gas in the loop 200, the inlet tube 201 and the outlet tube 202 are provided with respective one one-way valves 21 and 22.

A vaporizing filter 23 is located in the inlet tube 201 through which the respiratory gas flows and thereby vaporizes the liquid anaesthetic which is squirted into the vaporizing filter 23 from a vaporizing unit 24 via a vaporizing tube 204. An anaesthetic sensor 25 and a flow sensor 26 are respectively connected to a regulating device 27 via an anaesthetic signal line 210 and a flow signal line 211. The regulating device 27 can communicate with the ventilating control unit 3 via a two-way communication line 205, with the vaporizing unit 24 via a first control line 206 and with a fresh gas unit 28 via a second control line 207. The vaporizing unit 24 is connected to the regulating device 27 via a reference value line 208.

The fresh gas unit 28 is connected to the inlet tube 201 via a fresh gas tube 209 and allows fresh gas, e.g., oxygen, to be supplied to the inlet tube 201 to decrease the concentration level of anaesthetic in the respiratory gas. When awakening a patient it is preferable to quickly lower the concentration of anaesthetic. This is achieved by using the ventilating control unit 3 to empty the loop 200 of respiratory gas containing anaesthetic while the vaporizing unit 24 is switched off and the fresh gas unit fills the loop 200 with fresh gas. The fresh gas unit 28 may also supply oxygen to compensate for the uptake of oxygen by the patient. To increase the accuracy of maintenance of the oxygen level an oxygen sensor 29 is located in the inlet tube 201. Via an oxygen signal line 212 the oxygen sensor 29 is connected to the regulating device 27.

During use the patient unit 2 is first filled with the selected respiratory gas mixture by the ventilating control unit 3. Thereafter, the ventilating control unit 3 controls the inspiration and expiration. During inspiration one-way valve 22 blocks the flow so that the respiratory gas is forced into the inlet tube 201, through the carbon dioxide filter 20 and the vaporizing filter 23. As in the foregoing example, it is necessary to vaporize a larger amount of anaesthetic at the beginning of anaesthetization, which in this case requires a relatively large amount of liquid anaesthetic to be squirted into the vaporizing filter 23 via the vaporizing tube 204. To avoid a decrease in temperature, due to the vaporizing heat being taken from the filter 23 itself, the filter 23 is heated during the vaporization. The heating also facilitates the vaporization. In the regulating device 27 the reference value, transmitted through the reference value line 208, and the actual value of the concentration level of anaesthetic, transmitted through the anaesthetic signal line 210, are compared. The supply of liquid anaesthetic is then controlled by the regulating device 27 depending on the reference value and the actual value. In the same way the oxygen content of the respiratory gas is controlled by comparing a reference value, transmitted to the regulating device 27 by the communication line 205, with an actual value, measured by the oxygen sensor 29, and supplying a sufficient amount of oxygen into the inlet tube 201. The respiratory gas, with its content of anaesthetic, then continues through the one-way valve 21, into the patient tube 203 and into the patient's lungs 30.

During expiration the one-way valve 21 prevents the respiratory gas from passing through the inlet line 201. The respiratory gas is therefore conducted through one-way valve 22 out into the outlet tube 202 towards the ventilating control unit 3. When an expiration is completed the flow will reverse to inspiration and the cycle starts anew.

Although modifications and changes may be suggested by those skilled in the art, it is the intention of the inventors to embody within the patent warranted hereon, all changes and modifications as reasonably and properly come within the scope of their contribution to the art.

We claim as our invention:

1. An apparatus for the administration of a respiratory gas and at least one anaesthetic to a patient comprising:

means for conducting respiratory gas and said anaesthetic to said patient;

a vaporizing unit containing a liquid anaesthetic;

means for supplying respiratory gas to said vaporizing unit, said respiratory gas then passing through said vaporizing unit;

said vaporizing unit including means for vaporizing and entraining said liquid anaesthetic in said respiratory gas as said respiratory gas passes through said vaporizing means;

valve means in communication with said means for supplying respiratory gas and with said vaporizing unit for regulating the flow of said respiratory gas through said vaporizing unit;

further means for conducting said respiratory gas with said anaesthetic entrained therein from said vaporizing unit to said means for conducting respiratory gas and said anaesthetic to said patient;

reference means for providing a basic signal corresponding to a predetermined concentration of said anaesthetic; and control means connected to said reference means and to said valve means for controlling operation of said valve means to regulate the flow of said respiratory gas through said vaporizing means for substantially maintaining said predetermined concentration of said anaesthetic in said respiratory gas conducted to said patient.

2. An apparatus as claimed in claim 1, wherein said vaporizing unit includes thermal control means for controlling the temperature in said vaporizing unit and maintaining said temperature at a predetermined level.

3. An apparatus as claimed in claim 1, wherein said vaporizing unit includes a thermistor for measuring the temperature in said vaporizing unit and generating an electrical signal corresponding thereto, said thermistor being connected to said control means, said control means varying the flow of respiratory gas through said vaporizing unit dependent on said temperature.

4. An apparatus as claimed in claim 1, wherein the respiratory gas passes through the vaporizing unit so that the gas becomes saturated with anaesthetic.

5. An apparatus as claimed in claim 1, further comprising:

a first sensor disposed between said vaporizing unit and said patient for generating an electrical signal corresponding to a measured concentration of anaesthetic at said sensor, said first sensor being connected to said control means, said control means varying the flow of respiratory gas through said vaporizing unit dependent on said measured concentration.

6. An apparatus as claimed in claim 1, further comprising:

means for diverting a portion of said respiratory gas from said means for supplying respiratory gas around said vaporizing unit in a bypass path, and means for connecting said bypass path with said means for conducting respiratory gas and said anaesthetic to said patient for combining the diverted respiratory gas with said respiratory gas with said anaesthetic entrained therein.

7. An apparatus as claimed in claim 1, wherein said means for entraining said liquid anaesthetic in said respiratory gas comprises a wick to which liquid anaesthetic is provided, said respiratory gas passing through said wick and thereby entraining said liquid anaesthetic in said respiratory gas.

8. An apparatus as claimed in claim 1, further comprising flow sensor means disposed in said means for conducting said respiratory gas and said anaesthetic to the patient for generating an electrical signal corresponding to the total flow of respiratory gas and anaesthetic, said flow sensor means supplying said electrical signal to said control means, said control means varying the flow of respiratory gas through said vaporizing unit dependent on said measured total flow.

9. An apparatus as claimed in claim 8, wherein said control means is connected to said means for supplying respiratory gas to said conducting means and/or said vaporizing unit for regulating the supply of said respiratory gas to the patient so that the difference between the measured total flow of respiratory gas and anaesthetic to the patient and a predetermined value of the total flow is minimized.

10. An apparatus as claimed in caim 1, further comprising:
a source of fresh gas connected to said means for conducting said respiratory gas and said anaesthetic to the patient and operated by said control means for selectively supplying fresh gas to said patient without said fresh gas passing through said vaporizing unit.

11. An apparatus as claimed in claim 1, wherein said control means generates a control signal, said control signal being superimposed on said basic signal, said basic signal with said superimposed control signal being supplied to said valve means.

12. An apparatus as claimed in claim 1, wherein said control means is a microprocessor.

13. An apparatus as claimed in claim 1, further comprising:
a filter for absorption and desorption of said anaesthetic disposed in said means for conducting said respiratory gas and said anaesthetic to the patient.

14. An apparatus as claimed in claim 1, further comprising:
sensor means for measuring the concentration of said anaesthetic in said respiratory gas disposed in said means for conducting said respiratory gas with said anaesthetic to the airways of the patient; and
means connected to said sensor means for generating an alarm if the anaesthetic concentration at said sensor means is outside a predetermined range around said predetermined concentration.

15. An apparatus for the administration of respiratory gas and at least one anaesthetic to a patient comprising:
means for conducting and respiratory gas and said anaesthetic to said patient;
a vaporizing unit containing a liquid anaesthetic;
means for supplying respiratory gas to said vaporizing unit, said respiratory gas then passing through said vaporizing unit;
said vaporizing unit including means for vaporizing and entraining said liquid anaesthetic in said respiratory gas as said respiratory gas passes through said vaporizing unit;
further means for conducting said respiratory gas with said anaesthetic from said vaporizing unit to said means for conducting respiratory gas and said anaesthetic to said patient;
sensor means disposed in said means for conducting respiratory gas and said anaesthetic to said patient for generating an electrical signal corresponding to the amount of vaporized anaesthetic entrained in said respiratory gas;
reference means for providing a basic signal corresponding to a predetermined concentration of said anaesthetic; and
control means for regulating the vaporization of said liquid anaesthetic in said vaporizing unit so that the difference between the concentration of vaporized anaesthetic in said respiratory gas as measured by said sensor means and said predetermined concentration is minimized.

16. An apparatus as claimed in claim 15, wherein the respiratory gas passes through the vaporizing unit so that the gas becomes saturated with anaesthetic.

17. An apparatus as claimed in claim 15, further comprising:
means for diverting a portion of said respiratory gas from said means for supplying respiratory gas around said vaporizing unit in a bypass path, and means for connecting said bypass path with said means for conducting respiratory gas and said anaesthetic to said patient for combining the diverted respiratory gas with said respiratory gas with said anaesthetic entrained therein.

18. An apparatus as claimed in claim 15, wherein said vaporizing unit includes throttle valve means controlled by said control means for generating a pressure acting on said liquid anaesthetic which determines the amount of said liquid anaethetic which will be vaporized and entrained in said respiratory gas.

19. An apparatus as claimed in claim 15, wherein said vaporizing unit includes a filter to which said liquid anaesthetic is supplied, said liquid anaesthetic being vaporized and entrained by said respiratory gas passing through said filter.

20. An apparatus as claimed in claim 19, wherein said filter is disposed in said means for conducting said respiratory gas and said anaesthetic to the airways of said patient, and wherein said control means regulates the supply of said liquid anaesthetic to said filter so that only a minimally required amount of said liquid anaesthetic is supplied to said filter.

21. An apparatus as claimed in claim 19, further comprising a filter for the absorption and desorption of said anaesthetic disposed in said means for conducting said respiratory gas with said anaesthetic to the airways of said patient.

22. An apparatus as claimed in claim 15, further comprising:
flow sensor means disposed in said means for conducting said respiratory gas with said anaesthetic to the airways of said patient for measuring the total flow of said respiratory gas and said anaesthetic and generating an electrical signal corresponding to said total flow, said flow sensor means supplying said electrical signal to said control means for additional control of said vaporization of said liquid anaesthetic in said vaporizing unit dependent on said total flow.

23. An apparatus as claimed in claim 22, wherein said control means includes means for controlling said means for supplying respiratory gas to said vaporizing unit for minimizing a difference between said total flow as measured by said flow sensor means and a predetermined flow value.

24. An apparatus as claimed in claim 15, further comprising:
a fresh gas source connected to said means for conducting said respiratory gas with said anaesthetic to the airways of said patient, controlled by said control means for supplying fresh gas to said patient without passing through said vaporizing unit.

25. An apparatus as claimed in claim 15, wherein said control means generates a control signal, said control signal being superimposed on said basic signal, said basic signal with said superimposed control signal being supplied to said valve means.

26. An apparatus as claimed in claim 15, wherein said control means is a microprocessor.

27. An apparatus as claimed in claim 15, further comprising:

further sensor means for generating an electrical signal corresponding to the concentration of said liquid anaesthetic in said respiratory gas disposed in said means for conducting said respiratory gas with said anaesthetic to the airways of said patient; and alarm means for receiving said signal from said further sensor means and for generating an alarm if said anaesthetic concentration falls outside a designated range around a predetermined concentration value.

* * * * *